(12) United States Patent
Yoshii et al.

(10) Patent No.: US 8,980,320 B2
(45) Date of Patent: Mar. 17, 2015

(54) FILM COATING AGENT FOR SOLID PREPARATION, AND SOLID PREPARATION USING SAME

(75) Inventors: Ryoji Yoshii, Mishima (JP); Yuki Hayashi, Kamakura (JP); Yuki Fujisaki, Kamakura (JP)

(73) Assignee: Toray Industries, Inc. (JP)

( * ) Notice: Subject to any disclaimer, the term of this patent is extended or adjusted under 35 U.S.C. 154(b) by 223 days.

(21) Appl. No.: 13/510,050

(22) PCT Filed: Nov. 30, 2010

(86) PCT No.: PCT/JP2010/071305
§ 371 (c)(1),
(2), (4) Date: May 16, 2012

(87) PCT Pub. No.: WO2011/065551
PCT Pub. Date: Jun. 3, 2011

(65) Prior Publication Data
US 2012/0237575 A1    Sep. 20, 2012

(30) Foreign Application Priority Data
Nov. 30, 2009 (JP) ................................. 2009-271794

(51) Int. Cl.
*A61K 9/30* (2006.01)
*A61K 9/28* (2006.01)

(52) U.S. Cl.
CPC ............. *A61K 9/2813* (2013.01); *A61K 9/2866* (2013.01)
USPC ........... 424/475; 424/477; 424/480; 424/459; 424/460; 424/458; 424/417; 424/463; 424/490; 424/474; 514/781

(58) Field of Classification Search
CPC .................................................... A61K 9/2866
See application file for complete search history.

(56) References Cited

U.S. PATENT DOCUMENTS

| | | | |
|---|---|---|---|
| 5,885,617 A | 3/1999 | Jordan | |
| 2003/0064036 A1 | 4/2003 | Petereit et al. | |
| 2009/0196889 A1* | 8/2009 | Penhasi | 424/400 |

FOREIGN PATENT DOCUMENTS

| | | |
|---|---|---|
| EP | 0 805 177 B1 | 11/1997 |
| JP | 9-150484 A | 6/1997 |
| JP | 11-315222 A | 11/1999 |
| JP | 2002-012541 A | 1/2002 |
| JP | 2004-518750 A | 6/2004 |
| JP | 2008-201712 A | 9/2008 |
| JP | 2008-201713 A | 9/2008 |
| WO | 2004/073582 A2 | 9/2004 |
| WO | 2008/069262 A1 | 6/2008 |
| WO | 2010/074223 A1 | 7/2010 |

OTHER PUBLICATIONS

J.M. Lagarón et al., "High Water Barrier Nanobiocomposites of Methyl Cellulose and Chitosan for Film and Coating Applications," Journal of Plastic Film and Sheeting, vol. 25, No. 1, 2009, pp. 47-59.

* cited by examiner

*Primary Examiner* — Hasan Ahmed
(74) *Attorney, Agent, or Firm* — DLA Piper LLP (US)

(57) ABSTRACT

A film coating agent for a solid formulation includes a water-soluble cellulose derivative, swelling clay, a cationic surfactant, and a fatty acid, wherein mass ratio of the swelling clay to the water-soluble cellulose derivative is 2:8 to 8:2, and content of the cationic surfactant is not less than 0.5 equivalents and not more than 3.0 equivalents relative to a cation exchange equivalent of the swelling clay.

4 Claims, No Drawings

FILM COATING AGENT FOR SOLID PREPARATION, AND SOLID PREPARATION USING SAME

RELATED APPLICATIONS

This is a §371 of International Application No. PCT/JP2010/071305, with an international filing date of Nov. 30, 2010 (WO 2011/065551 A1, published Jun. 3, 2011), which is based on Japanese Patent Application No. 2009-271794, filed Nov. 30, 2009, the subject matter of which is incorporated by reference.

TECHNICAL FIELD

This disclosure relates to a film coating agent for a solid formulation (solid preparation) and a solid formulation using the same.

BACKGROUND

Many pharmaceuticals are unstable when exposed to water vapor, and it is known that when the pharmaceuticals are left to stand unpacked, the quality is reduced by moisture absorption, thereby not exerting expected medicinal effects and besides causing side effects in a patient who took them. Therefore, most of the commercially available pharmaceuticals, especially solid formulations, are designed to avoid direct contact with water vapor by being packaged with a packaging material such as a PTP (press through pack) sheet. In recent years, PTP sheets in which polyvinylidene chloride, which has excellent water vapor barrier properties (moisture resistance), is laminated have been developed and put into practice.

Examples of methods for improving the stability of a solid formulation itself to water vapor include sugar-coating the solid formulation and film-coating the solid formulation with a macromolecular substance. In the latter, polyvinyl alcohol and aminoalkyl methacrylate copolymer E (Eudragit EPO (registered trademark); Degussa) are known as a macromolecular substance that exhibits water vapor barrier properties and, recently, a film coating agent having a capability of trapping water vapor in a coating layer by dispersing a hygroscopic drug in a water-soluble cellulose derivative (JP 2008-201712 A), a film coating agent having improved moisture resistance performance due to the addition of soybean lecithin, which is hydrophobic, to polyvinyl alcohol (U.S. Pat. No. 5,885,617), and a film coating agent having improved moisture resistance performance due to the addition of stearic acid to aminoalkyl methacrylate copolymer E (JP 2004-518750 W) have been developed.

In the field of packaging films different from the pharmaceutical field, a packaging film in which an inorganic layered compound is dispersed in polyvinyl alcohol is known as a means for improving the water vapor barrier performance under high humidity (JP 11-315222 A and JP 09-150484 A). However, it requires achieving only the moisture resistance, and it does not require considering the safety and disintegration properties as a pharmaceutical after being taken.

On the other hand, at clinical sites or dispensing pharmacies, to prevent forgetting to take prescribed drugs or taking a wrong dose, one-dose packages, which are provided by taking each of a plurality of pharmaceuticals to be taken in one dose out of a packaging material such as a PTP sheet and putting them in one bag, have been widespread and precedently used from a perspective different from the above-described approach to improve the stability of a solid formulation itself to water vapor by film coating, that is, from the standpoint of patient friendliness. In addition, in Western countries, patients often subdivide a pharmaceutical taken out of a package such as a PTP sheet for storage in a pill case or the like, and therefore methods for improving the water vapor barrier properties of a solid formulation itself have been demanded.

However, pharmaceuticals packed in a one-dose package, although their stability to water vapor is ensured at a distribution level by packaging materials such as a PTP sheet, can cause quality deterioration of the pharmaceuticals because they are stored unpacked for a long period of time, for example, at clinical sites.

When sugar-coating or conventional film-coating is applied to a solid formulation, quality deterioration due to water vapor might be reduced to some extent. However, at present, sugar-coating cannot be applied to all the solid formulations because the operation process takes a long time and because the solid formulation after sugar-coating can be so excessively large that it is difficult to take it; and sufficient water vapor barrier performance cannot be exhibited under high humidity even by the conventional film-coating. Further, a film coating agent in the field of packaging films has not been used as a pharmaceutical additive because it is a laminated film with a substrate film such as polyvinyl chloride, and at present it cannot be applied directly to a solid formulation from the standpoint of safety.

Thus, it could be helpful to provide a film coating agent for a solid formulation, which has excellent water vapor barrier properties and is capable of stably maintaining the quality of medicinal ingredients even when the solid formulation has been stored unpacked for a long period of time.

SUMMARY

We discovered that a film coating agent in which swelling clay has a particular laminated structure in a water-soluble cellulose derivative exhibits water vapor barrier performance equivalent or superior to that of a PTP sheet (under the environment of 40° C. and 75% relative humidity, water vapor transmission: less than $1 \times 10^{-4}$ g·mm/cm$^2$·24 hr·atm).

Thus, we provide a film coating agent for a solid formulation, comprising a water-soluble cellulose derivative, swelling clay, a cationic surfactant, and a fatty acid, wherein the mass ratio of the above-described swelling clay to the above-described water-soluble cellulose derivative is 2:8 to 8:2, and the content of the above-described cationic surfactant is not less than 0.5 equivalents and not more than 3.0 equivalents relative to the cation exchange equivalent of the above-described swelling clay.

Film-coating a solid formulation with the above-described film coating agent provides a solid formulation with water vapor barrier performance equivalent or superior to that of a PTP sheet and allows coating with a thin film and, consequently, there will be no problem in taking the coated solid formulation.

The above-described water-soluble cellulose derivative is preferably hydroxypropylmethylcellulose (hypromellose), hydroxypropylcellulose, or methylcellulose. The above-described swelling clay is preferably bentonite or magnesium aluminum silicate. The above-described cationic surfactant is preferably benzalkonium chloride, benzethonium chloride, or distearyl dimethyl ammonium chloride. The above-described fatty acid is preferably stearic acid, capric acid, or oleic acid.

We also provide a solid formulation coated with the above-described film coating agent.

A solid formulation can be coated with a thin film and the coated solid formulation can be provided with water vapor barrier performance equivalent or superior to that of a PTP sheet. Therefore, coating a solid formulation with the film coating agent provides a solid formulation that is capable of stably maintaining the quality of medicinal ingredients even when the solid formulation has been stored unpacked for a long period of time and is suitable for one-dose package.

In addition, the film coating agent also has excellent disintegration properties and, therefore, it can also be applied to the coating not only of sustained-release formulations but also of immediate-release formulations. Further, the film coating agent can be used to coat a solid formulation using a coating equipments (for example, a continuous aeration coating equipment, a fluidized-bed coating equipment, a pan coater, and the like) commonly used in the field of pharmaceutical production and, therefore, it has extremely high versatility and convenience in coating operation.

DETAILED DESCRIPTION

Preferred coating agents and solid preparations will now be described. It should be understood that this disclosure is not limited to the following examples. Unless otherwise specified, "%" represents "mass/mass percentage (w/w %)."

The film coating agent for a solid formulation comprises a water-soluble cellulose derivative, swelling clay, a cationic surfactant, and a fatty acid; the mass ratio of the above-described swelling clay to the above-described water-soluble cellulose derivative is 2:8 to 8:2; and the content of the above-described cationic surfactant is not less than 0.5 equivalents and not more than 3.0 equivalents relative to the cation exchange equivalent of the above-described swelling clay.

"Film coating agent" refers to a composition that coats a solid formulation by forming a thin film on the surface of the solid formulation to prevent, for example, decomposition of medicinal ingredients due, for example, to oxygen, water vapor, or light. The film coating agent may be prepared by dispersing or dissolving each component in an appropriate solvent.

By, for example, applying or spraying the film coating agent to a solid formulation and removing the solvent by drying, a thin film can be formed on the surface of the solid formulation. Further, if the solvent is removed by drying after medicinal ingredients has been added directly to the film coating agent, a film formulation can also be obtained.

Examples of solvents for preparing the film coating agent include, for example, water, C1 to C5 chain alcohols (lower alcohols), or mixed solvents thereof, and water is preferred.

"Water-soluble cellulose derivative" refers to cellulose or a derivative thereof that can be uniformly dispersed or dissolved in water, lower alcohols, or mixed solvents thereof, examples of which include hydroxypropylmethylcellulose (hereinafter referred to as "HPMC"), hydroxypropylcellulose, methylcellulose, hydroxyethylcellulose, sodium carboxymethylcellulose, or mixtures thereof. HPMC, hydroxypropylcellulose, or methylcellulose is preferred, and HPMC is more preferred.

HPMC herein refers to a cellulose that is water-soluble derivatized by introducing hydroxypropoxyl groups and methyl groups into some hydroxyl groups of the cellulose, examples of which include various types of METOLOSE (registered trademark; Shin-Etsu Chemical Co., Ltd.) and Methocel (registered trademark; Dow Chemical Company).

The average viscosity at 20° C. of a 2% aqueous solution of HPMC is preferably 3 to 100000 cps, and more preferably 3 to 15 cps.

The degree of substitution of the hydroxypropoxyl groups and methyl groups in HPMC is preferably 4 to 12% and 19 to 30%, and more preferably 7 to 12% and 28 to 30%, respectively, based on the hydroxyl groups contained in the cellulose.

For HPMC, two or more HPMCs having different average viscosity at 20° C. of a 2% aqueous solution or different degree of substitution may be used in combination.

"Swelling clay" refers to a clay having swelling properties, and more particularly to a substance having swelling properties among finely-powdered substances that exhibit viscosity and plasticity when containing an appropriate amount of water.

As the swelling clay, those that are negatively charged because of the compositional balance of the metal salt species are preferred, and hydrated aluminum silicate having three-layer structure such as smectite is preferred.

"Negatively charged" refers to the state of the swelling clay when it has cation exchange properties, and the amount of charge is expressed as Cation Exchange Capacity (CEC). The unit of cation exchange capacity is milliequivalent/100 grams (hereinafter referred to as "meq/100 g" for short) and generally expressed as the number of equivalents which corresponds to the molar concentration of monovalent ions.

Examples of smectites include, for example, beidellite, nontronite, saponite, hectorite, sauconite, bentonite (hereinafter referred to as "BT"), magnesium aluminum silicate, or mixtures thereof. Magnesium aluminum silicate or BT is preferred, and BT is more preferred.

"Cationic surfactant" refers to a compound that has a lipophilic group portion and a hydrophilic group portion in the molecule and becomes positively charged by dissociation of the hydrophilic group portion into ions when dissolved in water.

As the "cationic surfactant", those that can be used in pharmaceuticals, foods, and cosmetics are preferred, examples of which include benzalkonium chloride, benzethonium chloride, distearyl dimethyl ammonium chloride, or mixtures thereof, and benzalkonium chloride and benzethonium chloride are more preferred.

"Fatty acid" refers to an organic acid that is a component, for example, of fats and oils, waxes, or lipids, and more particularly to a monovalent carboxylic acid compound of a long-chain hydrocarbon, the hydrocarbon moiety of which is linear, branched, or cyclic.

As the fatty acid, those that can be used in pharmaceuticals, foods, and cosmetics are preferred, examples of which include stearic acid, oleic acid, palmitin acid, capric acid, caprylic acid, myristic acid, arachidonic acid, linoleic acid, linolenic acid, palmitolic acid, myristoleic acid, or mixtures thereof. Stearic acid, oleic acid, palmitin acid, or capric acid is more preferred, and stearic acid is still more preferred.

"Solid formulation" refers to a preparation that is solid, examples of which include tablets (including sublingual tablets and orally disintegrating tablets), capsules (including soft capsules and microcapsules), granules, fine granules, powders, balls, troches, or films.

The swelling clay is preferably uniformly dispersed in the film formed from the above-described coating agent for a pharmaceutical solid formulation. "Uniformly dispersed" is most preferably the state in which the swelling clay is dispersed as a one-layer belt-like structure, but it is difficult to exfoliate the swelling clay to one layer with the production equipment commonly used for pharmaceutical production. Practically, the swelling clay is preferably dispersed as a belt-like laminated structure in which 10 to 100 layers of belt-like structures are laminated, and the number of lamination of the belt-like laminated structures is preferably smaller. This is because, in the film formed from the coating agent containing a certain amount of BT and polymer, uniform dispersion as a belt-like laminated structure with a smaller number of lamination provides a longer labyrinth effect and improves water vapor barrier performance.

In the cross section in the thickness direction of the film formed from the coating agent for a pharmaceutical solid formulation, the above-described belt-like laminated structure is preferably dispersed in a mesh pattern and planarly oriented. The state of the belt-like laminated structure in the cross section in the thickness direction of the film can be observed by using, for example, a transmission electron microscope (TEM).

"In a mesh pattern" refers to the situation where the belt-like structure of the swelling clay is forming literally a mesh when the dispersion state of the belt-like laminated structure in the cross section in the thickness direction of the film is expressed two-dimensionally.

"Planarly oriented" refers to the situation where the belt-like structure of the swelling clay is laminated in the thickness direction of the film.

For dispersing the swelling clay in the film formed from the coating agent for a pharmaceutical solid formulation as a belt-like laminated structure, the swelling clay contained in the coating agent is preferably in a swollen state.

"Swollen state" of the swelling clay refers to the state in which the swelling clay is swollen by containing a dispersion medium. Examples of swelling clay in a swollen state include, for example, a dispersion obtained by suspending swelling clay in a dispersion medium and stirring the suspension, for example, with a homogenizer, and it is preferable to be dispersed to the extent that all the swelling clay is able to pass through a filter paper when the dispersion is filtered. Examples of filter papers used in the above-described filtering operation include, for example, a glass fiber filter paper GF/D: particle holding capacity of 2.7 μm (Whatman).

When the mass ratio of the above-described swelling clay to the above-described water-soluble cellulose derivative is 2:8 to 8:2, a solid formulation can be provided with water vapor barrier performance equivalent or superior to that of a PTP sheet. The mass ratio is more preferably 3:7 to 8:2, and still more preferably 4:6 to 8:2.

The reason is that, when the value of the swelling clay in the above-described mass ratio is less than 2, the degree of entanglement between laminates of the swelling clay becomes low, and further the labyrinth effect of the swelling clay becomes small, whereby high water vapor barrier performance cannot be obtained; and when the value of the swelling clay in the above-described mass ratio is more than 8, laminates of the swelling clay can hardly be arranged in order, the unarranged parts resulting in structural defects, whereby high water vapor barrier performance cannot be obtained.

To obtain the labyrinth effect of the swelling clay sufficiently, the percentage of the swelling clay in the film formed from the above-described coating agent for a pharmaceutical solid formulation is preferably not less than 20%.

The water vapor transmission of the film formed from the coating agent for a pharmaceutical solid formulation is preferably $1.0 \times 10^{-5}$ to $1.0 \times 10^{-4}$ g·mm/cm$^2$·24 hr·atm, which is equivalent to that of a PTP sheet, more preferably $1.0 \times 10^{-5}$ to $6.5 \times 10^{-5}$ g·mm/cm$^2$·24 hr·atm, and still more preferably $1.0 \times 10^{-5}$ to $3.0 \times 10^{-5}$ g·mm/cm$^2$·24 hr·atm.

When the content of the above-described cationic surfactant is not less than 0.5 equivalents and not more than 3.0 equivalents relative to the cation exchange equivalent of the above-described swelling clay, a solid formulation can be provided with water vapor barrier performance equivalent or superior to that of a PTP sheet. The content is more preferably not less than 0.5 equivalents and not more than 2.0 equivalents, and still more preferably not less than 0.5 equivalents and not more than 1.5 equivalents, relative to the cation exchange equivalent of the above-described swelling clay.

The reason is that, when the content of the above-described cationic surfactant is less than 0.5 equivalents relative to the cation exchange equivalent of the swelling clay, electrostatic interaction between the swelling clay and the cationic surfactant becomes small, whereby sufficient water vapor barrier performance cannot be obtained.

The content of the above-described fatty acid is more preferably 0.2 to 2 equivalents relative to 1 equivalent of the cationic surfactant from the standpoint of uniform dispersion due to the coexistence with the cationic surfactant.

Examples of methods for coating a solid preparation with the above-described film coating agent include, for example, the use of a coating pan or a coating machine for tablets in the case where the solid preparation is in the form of tablets, and, for example, the use of a fluidized-bed coating machine or a rolling fluidized-bed coating machine in the case where the solid formulation is in the form of granules or powders.

To the above-described film coating agent, pharmaceutically acceptable additives may be added. When improving the disintegration properties of the film, for example, a saccharide and a sugar alcohol such as maltose, maltitol, sorbitol, xylitol, fructose, glucose, lactitol, isomaltose, lactose, erythritol, mannitol, trehalose, or sucrose; croscarmellose sodium; or low-substituted hydroxypropylcellulose can be added as a swelling disintegrant, and when improving the strength of the film, for example, triethyl citrate, polyethylene glycol, or glycerin can be added as a plasticizer.

To the above-described film coating agent, additives generally used for film coating in the pharmaceutical field may be further added, and examples of such additives include, for example, coloring agents such as dyes extracted from plants, titanium oxide, calcium carbonate, or silicon dioxide, which serve as a masking agent.

The solid formulation coated with the above-described film coating agent may be a solid formulation pre-coated, for example, with a gastric-soluble or enteric-soluble macromolecular substance. Further, the solid formulation coated with the film coating agent may be further coated with a film such as a gastric-soluble or enteric-soluble macromolecular substance.

EXAMPLES

Our coating agents and preparations will now be described specifically by way of examples, but the disclosure is not limited to thereto.

Method of Measuring Water Vapor Transmission of Film

Water vapor transmission, an indicator of the water vapor barrier performance of the film formed with the film coating agent was measured according to JIS K 8123 (1994) with minor modifications.

Specifically, the film formed with the film coating agent was cut, with light passing therethrough, selectively at a portion of uniform thickness without a pinhole into a circle with a diameter of 3.5 cm, and the thickness of the film was measured at arbitrary five points. Next, 3 g of calcium chloride (particle size: 850 to 2000 μm) was placed in an aluminum cup (diameter: 30 mm), and the film cut into a circle and a ring for fixing the film were sequentially placed on the aluminum cup. The ring was fixed by placing a weight on the ring, and in this state, molten paraffin wax was poured into the edge of the aluminum cup. After the paraffin wax was solidified, the weight was removed, and the mass of the whole aluminum cup was measured to determine the initial mass. Then, the aluminum cup was placed in a thermostat bath at 40° C. and 75% RH. The aluminum cup was taken out every 24 hours for measuring the mass to calculate the water vapor transmission coefficient by using the following equation. In all of the tests for measuring the water vapor transmission described below, r=1.5 cm; t=24 hours; and C=1 atm.

Water vapor transmission $P$ (g·mm/cm$^2$·24 hr·atm)= $(W \times A)/(B \times t \times C)$ W: Mass increased in 24 hours (g)
A: Mean value of film thickness at five points (mm)
B: Transmission area $\pi r^2$ (cm$^2$)
t: Elapsed time (hr)
C: Atmospheric pressure (atm)

Example 1

Benzalkonium chloride was added to distilled water and dissolved, and then the resulting mixture was heated to about 70° C. Stearic acid was added thereto and stirred, and the resulting mixture was uniformly dispersed. Thereafter, the dispersion obtained was allowed to cool to room temperature, and HPMC (METOLOSE (registered trademark) TC-5R; Shin-Etsu Chemical Co., Ltd.) was added thereto and dissolved to obtain a dispersion I.

BT (Kunipia-F (registered trademark); KUNIMINE INDUSTRIES CO. LTD., cation exchange capacity: 115 meq/100 g) was added to stirred distilled water. The resulting mixture was uniformly dispersed with a homogenizer (Polytron (registered trademark) Model KR), and then suction-filtered with a filter paper. The filtrate (BT water dispersion) obtained was taken as a dispersion II.

The dispersion I and the dispersion II were mixed and gelated by electrostatic interaction. After crush-stirring with a homogenizer, the resultant was suction-filtered with a filter paper to obtain a dispersion for single-spray film-forming.

The above-described dispersion for single-spray film-forming was sprayed onto the back of a polypropylene balance tray, and immediately dried with hot air from a dryer. Spraying and drying with the dryer were repeated several times, and then the balance tray was allowed to stand in an oven at 50° C. and dried overnight. Thereafter, a film was separated from the balance tray to form a film (hereinafter referred to as "the film of Example 1") by the single-spray film-forming method.

In the formulation of the above-described dispersion for single-spray film-forming, the formulation was carried out such that the mass ratio of BT to HPMC was BT:HPMC=7:3; benzalkonium chloride was 0.5 equivalents relative to the cation exchange equivalent of BT; and the fatty acid was 0.5 equivalents similarly to benzalkonium chloride that serves as a cationic surfactant. The formulation was carried out such that the solid content concentration of the dispersion I and II were both 3.2%.

Example 2

The dispersion I and the dispersion II described in Example 1 were prepared. The dispersion I was sprayed once onto the back of a polypropylene balance tray, following which the dispersion II was sprayed once onto the back of the same polypropylene balance tray, and they were immediately dried with hot air from a dryer. This operation was repeated several times, and then the balance tray was allowed to stand in an oven at 50° C. and dried overnight. Thereafter, a film was separated from the balance tray to form a film (hereinafter referred to as "the film of Example 2") by the dual-spray film-forming method in which two kinds of dispersions are alternately spray-coated.

Example 3

The same operation as in Example 1 was performed except that benzalkonium chloride in Example 1 was changed to benzethonium chloride to form a film (hereinafter referred to as "the film of Example 3").

Example 4

The same operation as in Example 1 was performed except that benzalkonium chloride in Example 1 was changed to distearyl dimethyl ammonium chloride to form a film (hereinafter referred to as "the film of Example 4").

Example 5

The same operation as in Example 1 was performed except that stearic acid in Example 1 was changed to oleic acid to form a film (hereinafter referred to as "the film of Example 5").

Example 6

The same operation as in Example 1 was performed except that stearic acid in Example 1 was changed to capric acid to form a film (hereinafter referred to as "the film of Example 6").

Comparative Example 1

The same operation as in Example 1 was performed except that the dispersion II was used in place of the dispersion for single-spray film-forming in Example 1 to form a film (hereinafter referred to as "the film of Comparative Example 1").

Comparative Example 2

The same operation as in Example 1 was performed except that dispersion for single-spray film-forming in Example 1 was changed to a 10% HPMC aqueous solution to form a film (hereinafter referred to as "the film of Comparative Example 2").

Comparative Example 3

The same operation as in Example 1 was performed except that the dispersion I in Example 1 was changed to a 3.2% HPMC aqueous solution to form a film (hereinafter referred to as "the film of Comparative Example 3").

Comparative Example 4

The same operation as in Example 1 was performed except that stearic acid was not added to the dispersion I in Example 1 to form a film (hereinafter referred to as "the film of Comparative Example 4").

Comparative Example 5

The same operation as in Example 1 was performed except that benzalkonium chloride was not added to the dispersion I in Example 1 to form a film (hereinafter referred to as "the film of Comparative Example 5").

Comparative Example 6

The same operation as in Example 1 was performed except that HPMC was not added to the dispersion I in Example 1 to form a film (hereinafter referred to as "the film of Comparative Example 6").

Comparative Example 7

The same operation as in Example 1 was performed except that BT in Example 1 was changed to light anhydrous silicic acid (AEROSIL (registered trademark); Nippon Aerosil Co., Ltd.) to form a film (hereinafter referred to as "the film of Comparative Example 7"). Since light anhydrous silicic acid does not have an ion-exchange capacity, both benzalkonium chloride and stearic acid were added in the same amount as in Example 1.

Comparative Example 8

The same operation as in Example 1 was performed except that stearic acid in Example 1 was changed to hardened oil (San-Ei Gen F.F.I., Inc.) to form a film (hereinafter referred to as "the film of Comparative Example 8").

Comparative Example 9

The same operation as in Example 1 was performed except that benzalkonium chloride in Example 1 was changed to polyoxyethylene.polyoxypropylene.glycol (Pluronic (registered trademark); Asahi Denka Kogyo K.K. Hereinafter, referred to as "POE.POP.glycol" for short) to form a film (hereinafter "the film of Comparative Example 9"). Since POE.POP.glycol is nonionic, both benzalkonium chloride and stearic acid were added in the same amount as in Example 1.

Evaluation of Water Vapor Transmission of Each Film

The measurement results of the water vapor transmission of each film obtained in Examples 1 to 6 and Comparative Examples 1 to 9 are shown in Table 1. In Film-forming method in Table 1, S means that the single-spray film-forming method was applied; and D means that the dual-spray film-forming method was applied.

TABLE 1

| Film | Inorganic particles | Water-soluble cellulose derivative | Inorganic particles/Water-soluble cellulose derivative (weight ratio) | Surfactant (0.5 eq.) | Hydrophobic substance (0.5 eq.) | Film forming method | Water vapor transmission (g · mm/ cm$^2$ · 24 hr · atm) |
|---|---|---|---|---|---|---|---|
| Ex. 1 | BT | HPMC | 7/3 | Benzalkonium chloride | Stearic acid | S | $7.3 \times 10^{-5}$ |
| Ex. 2 | BT | HPMC | 7/3 | Benzalkonium chloride | Stearic acid | D | $5.0 \times 10^{-5}$ |
| Ex. 3 | BT | HPMC | 7/3 | Benzethonium chloride | Stearic acid | S | $4.8 \times 10^{-5}$ |
| Ex. 4 | BT | HPMC | 7/3 | Distearyl dimethyl ammonium chloride | Stearic acid | S | $6.5 \times 10^{-5}$ |
| Ex. 5 | BT | HPMC | 7/3 | Benzalkonium chloride | Oleic acid | S | $5.9 \times 10^{-5}$ |
| Ex. 6 | BT | HPMC | 7/3 | Benzalkonium chloride | Capric acid | S | $3.4 \times 10^{-5}$ |
| Comp. Ex. 1 | BT | Absent | 10/0 | Absent | Absent | S | $4.3 \times 10^{-3}$ |
| Comp. Ex. 2 | Absent | HPMC | 0/10 | Absent | Absent | S | $6.0 \times 10^{-4}$ |
| Comp. Ex. 3 | BT | HPMC | 7/3 | Absent | Absent | S | $2.2 \times 10^{-4}$ |
| Comp. Ex. 4 | BT | HPMC | 7/3 | Benzalkonium chloride | Absent | S | $2.5 \times 10^{-4}$ |
| Comp. Ex. 5 | BT | HPMC | 7/3 | Absent | Stearic acid | S | $2.2 \times 10^{-4}$ |
| Comp. Ex. 6 | BT | Absent | 10/0 | Benzethonium chloride | Stearic acid | S | $3.7 \times 10^{-4}$ |
| Comp. Ex. 7 | Light anhydrous silicic acid | HPMC | 7/3 | Benzalkonium chloride | Stearic acid | S | $7.6 \times 10^{-4}$ |
| Comp. Ex. 8 | BT | HPMC | 7/3 | Benzalkonium chloride | Hardened oil | S | $6.4 \times 10^{-4}$ |
| Comp. Ex. 9 | BT | HPMC | 7/3 | POE•POP glycol | Stearic acid | S | $2.2 \times 10^{-4}$ |

In the case where light anhydrous silicic acid was used in place of swelling clay (Comparative Example 7), the case where hardened oil was used in place of fatty acid (Comparative Example 8), and the case where POE.POP.glycol was used in place of cationic surfactant (Comparative Example 9), the water vapor transmission of each film was not less than $1\times10^{-4}$ g·mm/cm$^2$·24 hr·atm, and the desired water vapor barrier performance could not be obtained. On the other hand, any of the water vapor transmission of the films formed with our film coating agent was less than $1\times10^{-4}$ g·mm/cm$^2$·24 hr·atm. From the results in Table 1 as shown above, it became apparent that our film coating agent containing as an essential component a water-soluble cellulose derivative, swelling clay, a cationic surfactant, and a fatty acid can provide a solid formulation with significant water vapor barrier performance at the same level as that of PTP packaging materials. No great difference in water vapor transmission was observed depending on the film-forming method (the single-spray film-forming method (Example 1) or the dual-spray film-forming method (Example 2)).

Examples 7 to 13 and Comparative Example 10, Comparative Example 11

The same operation as in Example 1 was performed except that the mass ratio of BT to HPMC in Example 1 was changed to the values in Table 2 to form a film of Examples 7 to 13 and Comparative Examples 10 and 11 (hereinafter referred to as "the film of Example 7," "the film of Example 8," "the film of Example 9," "the film of Example 10," "the film of Example 11," "the film of Example 12," "the film of Example 13," "the film of Comparative Example 10," and "the film of Comparative Example 11," respectively).

Discussion of the Mass Ratio of BT:HPMC

The water vapor transmission of each film obtained in Examples 7 to 13 and Comparative Examples 10 and 11 was measured individually, and the results are shown in Table 2.

TABLE 2

| Film | BT/HPMC (weight ratio) | Benzalkonium chloride (Equivalents per cation exchange equivalent of BT) | Stearic acid (Equivalents per cation exchange equivalent of BT) | Water vapor transmission (g·mm/cm$^2$·24 hr·atm) |
|---|---|---|---|---|
| Comp Ex. 10 | 1/9 | 0.5 | 0.5 | $2.0 \times 10^{-4}$ |
| Ex. 7 | 2/8 | 0.5 | 0.5 | $9.3 \times 10^{-5}$ |
| Ex. 8 | 3/7 | 0.5 | 0.5 | $6.5 \times 10^{-5}$ |
| Ex. 9 | 4/6 | 0.5 | 0.5 | $4.5 \times 10^{-5}$ |
| Ex. 10 | 5/5 | 0.5 | 0.5 | $4.4 \times 10^{-5}$ |
| Ex. 11 | 6/4 | 0.5 | 0.5 | $3.5 \times 10^{-5}$ |
| Ex. 12 | 7/3 | 0.5 | 0.5 | $3.1 \times 10^{-5}$ |
| Ex. 13 | 8/2 | 0.5 | 0.5 | $2.7 \times 10^{-5}$ |
| Comp. Ex. 11 | 9/1 | 0.5 | 0.5 | $3.1 \times 10^{-4}$ |

From the results in Table 2, it became apparent that when the mass ratio of BT to HPMC is in the range of BT:HPMC=2:8 to 8:2, the water vapor transmission of the film is less than $1\times10^{-4}$ g·mm/cm$^2$·24 hr·atm, which allows providing a solid formulation with significant water vapor barrier performance at the same level as that of PTP packaging materials.

Examples 14 to 18 and Comparative Example 12, Comparative Example 13

The same operation as in Example 1 was performed except that the equivalent of benzalkonium chloride and stearic acid in Example 1 was changed to the values in Table 3 to form a film of Examples 14 to 18 and Comparative Example 12 (hereinafter referred to as "the film of Example 14," "the film of Example 15," "the film of Example 16," "the film of Example 17," "the film of Example 18," and "the film of Comparative Example 12," respectively). The film could not be formed by the operation in Comparative Example 13.

Discussion of the Number of Equivalents of Cationic Surfactant and Fatty Acid Relative to Cation Exchange Equivalent of BT The measurement results of the water vapor transmission of each film obtained in Examples 14 to 18 and Comparative Example 12 are shown in Table 3.

TABLE 3

| Film | BT/HPMC (weight ratio) | Benzalkonium chloride (Equivalents per cation exchange equivalent of BT) | Stearic acid (Equivalents per cation exchange equivalent of BT) | Water vapor transmission (g·mm/cm$^2$·24 hr·atm) |
|---|---|---|---|---|
| Comp. Ex. 12 | 7/3 | 0.1 | 0.1 | $1.3 \times 10^{-4}$ |
| Ex. 14 | 7/3 | 0.5 | 0.5 | $3.1 \times 10^{-5}$ |
| Ex. 15 | 7/3 | 1.0 | 1.0 | $1.4 \times 10^{-5}$ |
| Ex. 16 | 7/3 | 1.5 | 1.5 | $2.0 \times 10^{-5}$ |
| Ex. 17 | 7/3 | 0.5 | 0.1 | $5.5 \times 10^{-5}$ |
| Ex. 18 | 7/3 | 0.5 | 1.0 | $3.4 \times 10^{-5}$ |
| Comp. Ex. 13 | 7/3 | 0.5 | 1.5 | Stearic acid precipitated |

From the results in Table 3, it became apparent that when the amount of benzalkonium chloride is not less than 0.5 equivalents relative to the cation exchange equivalent of BT, the water vapor transmission of the film is less than $1\times10^{-4}$ g·mm/cm$^2$·24 hr·atm, which allows providing a solid formulation with significant water vapor barrier performance at the same level as that of PTP packaging materials.

In addition, also from the results in Table 3, it became apparent that when the amount of stearic acid is not less than 0.1 equivalents relative to the cation exchange equivalent of BT, the water vapor transmission of the film is less than $1\times10^{-4}$ g·mm/cm$^2$·24 hr·atm, which allows providing a solid formulation with significant water vapor barrier performance at the same level as that of PTP packaging materials. However, in the case where the amount of stearic acid was more than 2 equivalents relative to 1 equivalent of benzalkonium chloride that serve as a cationic surfactant (Comparative Example 13), the precipitation of stearic acid in the dispersion I was observed, uniform dispersion could not be achieved, and the film could not be formed.

Example 19

The same operation as in Example 1 was repeated to prepare a dispersion for single-spray film-forming, which was used as a dispersion for coating tablets.

To a coating pan (DRC-200; powrex corp.), 200 g of sodium valproate tablets (Depakene (registered trademark): 200 mg; Kyowa Hakko Kirin Co., Ltd.) were fed, and the tablets were coated with the above-described dispersion for coating tablets such that the thickness was 20 μm to obtain a coated solid formulation (hereinafter referred to as "the tablets of Example 19").

Comparative Example 14

Sodium valproate tablets (Depakene (registered trademark): 200 mg; Kyowa Hakko Kirin Co., Ltd.) were used as it were as a solid formulation for comparison (hereinafter referred to as "the tablets of Comparative Example 14").

Comparative Example 15

Sodium lauryl sulfate (15 g) was added to distilled water (875 g), and the resulting mixture was stirred for complete dissolution. Next, aminoalkyl methacrylate copolymer E (Eudragit EPO (registered trademark); Degussa) (100 g) was added, and the resulting mixture was stirred When this was uniformly dispersed, stearic acid (10 g) was added thereto, and the resulting mixture was further stirred to obtain a coating solution.

To a coating pan (DRC-200; powrex corp.), 200 g of sodium valproate tablets (Depakene (registered trademark): 200 mg; Kyowa Hakko Co., Ltd.) were fed, and the tablets were coated with the above-described coating solution such that the thickness was 20 μm to obtain a solid formulation for comparison (hereinafter referred to as "the tablets of Comparative Example 15").

Evaluation of Water Vapor Barrier Performance Using Drug-Containing Model Tablets Each tablet obtained in Example 19, Comparative Example 14, and Comparative Example 15 was left to stand under the conditions of 40° C. and 75% RH, and the deliquescence (appearance change) was observed over time. The results are shown in Table 4.

TABLE 4

| Tablets | Deliquescence of sodium valproate tablets | |
|---|---|---|
| | 1-day storage | 20-day storage |
| Ex. 19 | No appearance change | No appearance change |
| Comp. Ex. 14 | Tablets deliquesced | Tablets deliquesced |
| Comp. Ex. 15 | Tablets deliquesced | Tablets deliquesced |

From the results in Table 4, it became apparent that, in the existing tablets (the tablets of Comparative Example 14) and the tablets coated with a known moisture-proof film (the tablets of Comparative Example 15), the deliquescence of the tablets was observed after 1-day storage, whereas, in the tablets coated with our water vapor-barriering film coating (the tablets of Example 19), suppression of the deliquescence of sodium valproate was achieved, which allowed providing a solid formulation (model tablets) with significant water vapor barrier performance at the same level as that of PTP packaging materials.

INDUSTRIAL APPLICABILITY

Our film coating agent can be suitably used in the pharmaceutical field, especially as a film for a solid formulation containing a drug unstable to water vapor.

The invention claimed is:

1. A film coating agent for a solid formulation, comprising a hydroxypropylmethylcellulose, negatively charged swelling clay, a cationic surfactant, and a fatty acid, wherein mass ratio of said swelling clay to said hydroxypropylmethylcellulose is 2:8 to 8:2, and content of said cationic surfactant is not less than 0.5 equivalents and not more than 1.5 equivalents relative to a cation exchange equivalent of said swelling clay and content of said fatty acid is not less than 0.2 equivalents and not more than 2.0 equivalents relative to 1 equivalent of said cationic surfactant, wherein said cationic surfactant is benzalkonium chloride, benzethonium chloride or distearyl dimethyl ammonium chloride, and said fatty acid is stearic acid, capric acid, or oleic acid.

2. The film coating agent according to claim 1, wherein said negatively charged swelling clay is bentonite or magnesium aluminum silicate.

3. A solid formulation coated with the film coating agent according to claim 1.

4. A solid formulation coated with the film coating agent according to claim 2.

* * * * *